(12) United States Patent
Seiki et al.

(10) Patent No.: US 8,377,696 B2
(45) Date of Patent: Feb. 19, 2013

(54) HIGHLY SENSITIVE METHOD FOR DETECTING PROTEIN IN FOOD

(75) Inventors: Kosuke Seiki, Ibaraki (JP); Hiroshi Oda, Ibaraki (JP); Hisashi Yoshioka, Ibaraki (JP); Hiroshi Akiyama, Tokyo (JP); Tamio Maitani, Tokyo (JP)

(73) Assignees: Maruha Nichiro Seafoods, Inc., Tokyo (JP); Japan as Represented by Director General of National Institute of Health Sciences, Tokyo (JP)

( * ) Notice: Subject to any disclaimer, the term of this patent is extended or adjusted under 35 U.S.C. 154(b) by 283 days.

(21) Appl. No.: 12/594,867

(22) PCT Filed: Apr. 4, 2008

(86) PCT No.: PCT/JP2008/056754
§ 371 (c)(1),
(2), (4) Date: Oct. 6, 2009

(87) PCT Pub. No.: WO2008/126780
PCT Pub. Date: Oct. 23, 2008

(65) Prior Publication Data
US 2010/0112709 A1    May 6, 2010

(30) Foreign Application Priority Data

Apr. 6, 2007 (JP) ................................. 2007-101121

(51) Int. Cl.
*G01N 33/02* (2006.01)
*G01N 33/53* (2006.01)
*G01N 33/68* (2006.01)

(52) U.S. Cl. ............................. 436/20; 435/7.1; 436/86
(58) Field of Classification Search ......................... None
See application file for complete search history.

(56) References Cited

FOREIGN PATENT DOCUMENTS

WO    WO 01/34186 A1    5/2001

OTHER PUBLICATIONS

Fujita et al. "Enzyme-linked immunosorbent assay for anti-tropomyosin antibodies and its clinical application to various heart diseases" Clinica Chimica Acta 299 (2000) 179-192.*
Aalberse et al. "Cross-reactivity of IgE antibodies to allergens" Allergy 2001: 56: 478-490.*
Reese et al. "Reduced Allergenic Potency of VR9-1, a Mutant of the Major Shrimp Allergen Pen a 1 (Tropomyosin)" J Immunol 2005;175;8354-8364.*
Shiomi Kazuo, "Gyokairui Allergen no Tokutei, Kogen Kosa • Ichiji Kozo no Kaimei Oyobi Kenchi Kit no Kaihatsu", Buntan Kenkyu Hokokusho, pp. 33 to 46, (2006).
Shibahara Hiroaki, et al., "ELISA-ho o Mochiita Kkakurui Kenshtsu Shiyaku no Kaihatus (Development of reagent for detecting Crustacea using ELISA method)", Meeting of the Food Hygiene Society of Japan, vol. 92, p. 135, (2006).
Shinizu Kosuke, et al., "Kako Shokuhinchu no Kokakurui Tanpakushitsu Kenshutsuho no Kaihatsu ni Tsuite (Development of a method of detecting proteins of Crustacea in processed foods)", Meeting of the Food Hygiene Society of Japan, vol. 92, p. 134, (2006).
Fuller, H.R., et al., "An enzyme-linked immunosorbent assay (ELISA) for the major crustacean allergen, tropomyosin, in food", Food and Agricultural Immunology, vol. 17, No. 1-4, pp. 43-52, (2006).
Seiki, Kosuke et al., "A Reliable and Sensitive Immunoassay for the Determination of Crustacean Protein in Processed Foods", Journal of Agricultural and Food Chemistry, vol. 55, No. 23, pp. 9345-9350, Nov. 14, 2007.
Byeoung-Ju Jeoung. et al., "Quantification of the major brown shrimp allergen Pen a 1 (tropomyosin) by a monoclonal antibody-based sandwich ELISA", Journal of Allergy and Clinical Immunology, vol. 100, No. 2, XP-005189321, Aug. 1, 1997, pp. 229-234.

* cited by examiner

*Primary Examiner* — Christine Foster
(74) *Attorney, Agent, or Firm* — Oblon, Spivak, McClelland, Maier & Neustadt, L.L.P.

(57) ABSTRACT

A method for accurate and precise measurement of target proteins such as food allergen proteins in the specific foods is provided. The method is a method for immunological measurement of a food allergen protein in a processed food using an antibody against the food allergen protein, comprising adding animal tropomyosin to an assay solution upon measurement.

3 Claims, 11 Drawing Sheets

HIGHLY SENSITIVE METHOD FOR DETECTING PROTEIN IN FOOD

CROSS-REFERENCE TO RELATED APPLICATIONS

This application is a National Stage of PCT/JP08/056754 filed Apr. 4, 2008 and claims the benefit of JP 2007-101121 filed Apr. 6, 2007.

TECHNICAL FIELD

The present invention relates to a method for measuring a specific protein, such as an allergen protein in a food.

BACKGROUND ART

Upon detection of a specific protein in a food, the recovery rate in the additive test and dilution linearity are not guaranteed because of strong effects of food matrix ingredients other than a target proteins contained in the food, so that appropriate detection may be difficult. Particularly when a target is a muscle protein and animal proteins are further contained as matrices in the food, the target protein and the animal proteins may form complexes. Difficulty of the appropriate detection of a target is pronounced in these cases.

In recent years, health harm cases due to foods containing allergic substances (hereinafter, referred to as allergens) have been increasingly common. A questionnaire in a research report produced by a Committee on Measures against Food Allergy has revealed that 12.6% of nursery school toddlers, 8.6% of 3-year-old children, 7.4% of first-graders, 6.3% of junior high-school students, and 9.3% of adults have some of allergic symptom. In response to the results, since April 2001 (and effective starting in April 2002) the Ministry of Health, Labour and Welfare has enforced labeling system for five specific raw materials (eggs, milk, buckwheat noodles, wheat, and peanuts, which are specific raw materials with high number of patients and high severity) used for processed foods in order to provide information about these food materials to the allergic patients and to avoid health hazards. At the same time, notification has been given regarding detection methods for the purpose of realizing appropriate labeling.

In these methods for detecting allergens, surfactants and reducing agents are used to extract allergens as measurement targets efficiently from processed foods (see Patent Document 1 and Non-Patent Documents 1 and 2). However, these protein denaturants are also involved in the formation of complexes as described above, making appropriate measurement difficult.

It has been difficult to measure target specific proteins accurately and precisely in processed foods containing various food matrices as described above.

Patent Document 1: JP Patent No. 3600231
Non-Patent Document 1: Watanabe Y. et al.: Journal of Immunological Methods 300 (2005) 115-123
Non-Patent Document 2: Dept. of Food Safety, Pharmaceutical and Food Safety Bureau, Ministry of Health, Labour and Welfare, Notice (Shokuhatsu) No. 1106001 (Attachment 1, Nov. 6, 2002 (Final revision: Jun. 22, 2006); Notice (notification given by the Department of Food Safety) No. 0622003

DISCLOSURE OF THE INVENTION

Object to be Achieved by the Invention

An object of the present invention is to provide a method for accurately and precisely measuring a specific protein, such as a target food allergen protein, in a processed food without any food matrix effects.

Means for Achieving the Object

The present invention relates to an immunological method for detection of a specific protein in a food, which enables accurate and precise measurement by mixing a target protein with a protein of an organism differing from the origin of the target protein, when a calibration standard solution and a sample are diluted. Specifically, for example, when Crustacean tropomyosin, which is a major Crustacean allergen, is detected in a processed food, a calibration standard solution and a sample are diluted with a solution containing tropomyosin from another species having no antigenic cross-reactivity with Crustacean tropomyosin. With the use of such a diluted solution, measurement has been carried out by sandwich ELISA (enzyme-linked immunosorbent assay) constructed using a Crustacean tropomyosin-specific antibody, resulting in improved recovery of additive test and dilution linearity of tropomyosin, the target protein.

The present invention relates to the following [1] to [21].

[1] A method for immunological measurement of a specific protein in a processed food with the use of an antibody against the protein, comprising adding animal tropomyosin having no antigen cross-reactivity with the specific protein to be measured to an assay solution upon measurement and then measuring the specific protein.

[2] The method according to [1], which is a method for immunological measurement of a specific protein that is a food allergen protein in a processed food with the use of an antibody against the food allergen protein, comprising adding animal tropomyosin having no antigenic cross-reactivity with the specific protein to be measured to an assay solution upon measurement and then measuring the specific protein.

[3] The method according to [1] or [2], comprising extracting a food allergen protein from a processed food using an extraction solution containing a surfactant and a reducing agent, reacting the extracted food allergen protein with the antibody against the food allergen protein in the presence of animal tropomyosin, and then measuring the food allergen protein.

[4] The method according to [2] or [3], wherein the food allergen protein in the processed food is tropomyosin.

[5] The method according to [4], wherein the food allergen protein in the processed food is Crustacea-derived tropomyosin.

[6] The method according to any one of [1] to [5], wherein the concentration of animal tropomyosin contained in the assay solution upon measurement ranges from 0.001% to 0.040%.

[7] The method according to any one of [1] to [6] for immunological measurement of a specific protein in a processed food with the use of an antibody against the protein, wherein the recovery in the additive test and dilution linearity of the detected protein are improved through addition of animal tropomyosin having no antigenic cross-reactivity with the specific protein to be measured to an assay solution upon measurement.

[8] The method according to [7] for immunological measurement of a specific protein that is a food allergen protein in a processed food with the use of an antibody against the food allergen protein, wherein the recovery in the additive test and dilution linearity of the detected food allergen protein are improved through addition of animal tropomyosin having no antigenic cross-reactivity with the specific protein to be measured to an assay solution upon measurement.

[9] The method according to any one of [1] to [8], wherein tropomyosin is swine tropomyosin.

[10] The method according to any one of [1] to [8], wherein tropomyosin is purified tropomyosin.

[11] The method according to [10], wherein tropomyosin is purified swine tropomyosin.

[12] A reagent composition for dilution and preparation of a specific protein extracted from a processed food upon measurement of the specific protein in the processed food, comprising animal tropomyosin having no antigenic cross-reactivity with the specific protein to be measured.

[13] The reagent composition for dilution and preparation of a protein in a processed food according to [12], which is: a reagent composition for dilution and preparation of a specific protein that is a food allergen protein extracted from the processed food upon measurement of the food allergen protein in the processed food; and is a reagent composition for dilution and preparation of the food allergen protein containing animal tropomyosin.

[14] The reagent composition for dilution and preparation of a protein in a processed food according to [13], wherein the food allergen protein in the processed food is tropomyosin.

[15] The reagent composition for dilution and preparation of a protein in a processed food according to [14], wherein the food allergen protein in a processed food is Crustacea-derived tropomyosin.

[16] The reagent composition for dilution and preparation of a protein in a processed food according to any one of [12] to [15], which is prepared so that the concentration of animal tropomyosin contained in an assay solution upon measurement ranges from 0.001% to 0.040%.

[17] The reagent composition for dilution and preparation of a protein in a processed food according to any one of [12] to [16], wherein tropomyosin is swine tropomyosin.

[18] The reagent composition for dilution and preparation of a protein in a processed food according to any one of [12] to [16], wherein tropomyosin is purified tropomyosin.

[19] The reagent composition for dilution and preparation of a protein in a processed food according to [18], wherein tropomyosin is purified swine tropomyosin.

[20] A kit for measurement of a protein in a processed food, comprising the reagent composition for dilution and preparation of a protein in a processed food according to any one of [12] to [19] and an antibody against the protein in the processed food.

[21] The kit for measurement of a protein in a processed food according to [20], wherein the protein in the processed food is a food allergen.

EFFECTS OF THE INVENTION

According to the method of the present invention, a protein such as an allergen in a processed food can be appropriately measured and the content of a protein such as an allergen in a processed food can be appropriately measured.

This description includes part or all of the contents as disclosed in the description and/or drawings of Japanese Patent Application No. 2007-101121, which is a priority document of the present application.

PREFERRED EMBODIMENTS OF THE INVENTION

Figure 1A:
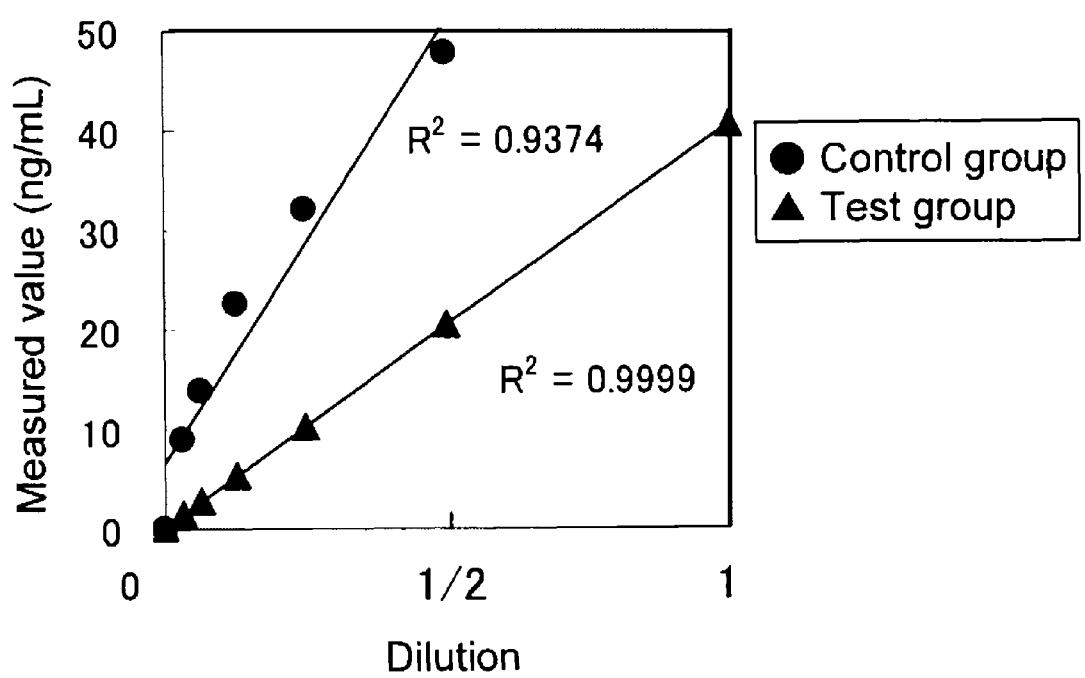
FIG. 1A shows the relationship between dilution rates and measured values when an extract of a fish sausage specimen was subjected to 2-fold serial dilution in a test using an extract of Alaska pollack minced fish fresh as a muscle tissue-derived protein.

Hereafter, the present invention is described in detail.

In the present invention, examples of foods to be measured include processed foods containing animal-derived meat and processed foods containing plants. Examples of animals include animals belonging to mammals, birds, fishes, Crustacea, Mollusc, or the like. Also, foods containing milk or avian eggs for foods are also examples of foods to be measured according to the present invention. Examples of plants to be measured according to the present invention include rice, cereals such as wheat, miscellaneous cereals such as buckwheat, pulses such as soybean, flours such as cereal flour and bean flour, starches, fruits, and vegetables.

Examples of processed foods specified under the Calibration Standard solution Commodity Classification for Japan include agricultural processed foods (Classification Code 72, processed vegetable products, noodles•breadstuffs, processed cereal products, and confectioneries, for example), processed livestock foods (Classification Code 73, meat products, dairy products, and processed egg products, for example), processed seafoods (Classification Code 74, processed fish and shellfish and processed seaweeds), other food articles (Classification Code 75, flavoring materials, soups, and prepared foods), beverages, ice, and manufactured tobacco (Classification Code 76, alcohol-free beverages, for example). Specific examples of the same include processed foods containing shrimp, crab, or the like. More preferred examples of the same that can be subjected to measurement include foods such as shrimp Shaomai, shrimp gratin, shrimp-containing snacks, shrimp pilaf, crab Kamaboko (boiled fish sausage), and crab cream croquette.

Examples of specific proteins in processed foods to be measured include, but are not limited to, muscle proteins contained in the above foods or proteins that can be allergens for humans. As such proteins described above, examples of muscle proteins include myofibrillary proteins such as actin, myosin, troponin, tropomyosin, M-protein, C-protein, F-protein, I-protein, actinin, filamin, Z protein, and desmin, sarcoplasmic proteins such as creatine kinase, parvalbumin, and myoglobin, and proteins of myostromas such as collagen and elastin. Furthermore, an example of a protein that can be an allergen for humans is tropomyosin contained in Crustacea such as shrimp and crab or Molluscs. Furthermore, other examples of the same include, but are not limited to, ovalbumin, ovomucoid, and the like contained in eggs, caseins ($\alpha$s1, $\alpha$s 2, $\beta$, and $\gamma$), lacto-albumin and the like contained in milk, glutenin, gliadin, and the like contained in wheats, actinidine and the like contained in fruits or vegetables, Ara h1, Ara h2, and the like contained in peanuts, bovine serum albumin (BSA) and the like contained in beef, Ses i 1 and the like contained in sesami, parvalbumin and the like contained in fishes, Giym Bd 30K and the like contained in soybean, and gelatin. Every food ingredients that cause allergic symptoms as food allergies in humans can be subjected to measurement according to the present invention.

A protein is extracted from a food to be subjected to measurement and then measured. Protein extraction is carried out by homogenizing a food using a blender, a homogenizer, a food cutter, or the like, adding a reagent for extraction, and then allowing the resultant slurry to stand for several hours to dozen hours or shaking the resultant slurry for several hours to dozen hours. A reagent for extraction to be used herein is not limited and saline or a buffer can be used, for example. As a buffer, a Tris buffer or a phosphate buffer may be used, which may further contain NaCl or serum albumin such as BSA. Moreover, for efficient extraction, a surfactant such as SDS (sodium dodecyl sulfate) or Tween20 and a reducing agent such as mercaptoethanol (2-ME) or dithiothreitol (DTT) are preferably contained. In this case, 5 mL to 50 mL, preferably 10 mL to 30 mL, and further preferably 15 mL to 25 mL of a reagent for extraction may be added per gram of a food. Furthermore, as a reagent for allergen extraction, a commercially available reagent for extraction of a specific raw material (Morinaga Institute of Biological Science, Inc. FASPEK/Extraction Reagent For Specified Ingredient, Watanabe et al., Journal of Immunological Methods 300 (2005) 115-123, composition: tris buffer containing BSA, SDS, and 2-ME) may also be used. In this case, 19 mL of the reagent for extraction of a specific raw material may be added per gram of a food. After extraction, centrifugation is carried out to recover a supernatant and then the thus obtained supernatant is used for measurement. In this case, a supernatant is preferably filtered using filter paper.

A protein in a supernatant may be measured by an immunoassay using an antibody against the protein to be measured. For example, when a protein to be measured is tropomyosin, an anti-tropomyosin antibody is used. When a protein to be measured is Crustacean tropomyosin, an antibody specific to Crustacean tropomyosin may be used. In this case, an absorbed antibody prepared via absorption of a polyclonal antibody with the use of a specific antigen may be used to enhance specificity, a monoclonal antibody having high specificity may be used, or a combination of polyclonal and monoclonal antibodies may be used.

In the present invention, when the above protein to be measured is extracted from the above specific food to be measured and is then measured, a muscle tissue-derived protein is added to the protein to be measured. As such muscle tissue-derived protein, an animal-derived muscle tissue protein is used. Such animal is preferably of species differing from that of the protein to be measured. Animal-derived muscle tissue proteins may be vertebrate-derived muscle tissue proteins such as fishes including bony fishes and cartilagenous fishes, mammals, amphibians, reptiles, or birds. Animal-derived muscle tissue proteins may also be derived from invertebrata such as Molluscs, Protochordata, Echinodermata, Coelenterata, or Arthropoda. Here, such animal species should differ from that of the protein to be measured. When Crustacea-derived protein is measured, examples of muscle tissue proteins to be used herein include muscle tissue proteins from fishes such as Alaska pollack or muscle tissue proteins from mammals such as pigs. At this time, when muscle tissue-derived proteins that are added upon measurement of a protein to be measured include a protein homologous to the protein to be measured, cross-reactivity may be observed in an immunoassay such as ELISA. Therefore, a muscle tissue protein that can be used in this case is derived from an animal species differing from that of a protein to be measured and does not show immunological cross-reactivity with the protein to be measured. Hence, such a muscle tissue protein having no antigenic cross-reactivity is added. Also, for example, a muscle tissue-derived protein to be added may be caused to contain no protein homologous to a protein to be measured through the use of such protein to be measured differing from the muscle tissue-derived protein to be added. Muscle tissues are collected from an animal listed above and then the muscle tissue-derived protein can be extracted. For example, when a muscle tissue protein from fishes such as Alaska pollack is used, a minced fish flesh extract, an extract of dry powder of minced fish flesh, or the like can be used. Isolation and purification of a muscle tissue-derived protein that is used in the present invention is not always required, and such a muscle tissue-derived protein may be added as a muscle tissue extract. Alternatively, a purified form of a muscle protein such as actin, myosin, troponin, tropomyosin, M-protein, C-protein, F-protein, I-protein, actinin, filamin, Z protein, desmin, creatine kinase, parvalbumin, myoglobin, collagen, or elastin may be used. In addition, when a muscle tissue-derived protein is added, an additive may be contaminated with another protein such as a blood protein, as long as the muscle tissue-derived protein is mainly contained in the additive. Therefore, a protein may be extracted from animal meat and then added.

A muscle tissue-derived protein is extracted by adding muscle tissue homogenized using a blender, a homogenizer, a food cutter, or the like, or adding muscle tissue pulverized after freeze-drying to a reagent for extraction and then allowing the resultant slurry to stand for several hours to dozen hours or shaking the resultant slurry for several hours to dozen hours. The temperature for extraction is not particularly limited. Extraction can be carried out at 4° C., room temperature, and 37° C., for example. A reagent for extraction, which is used herein, is not particularly limited. For example, saline or a buffer can be used. As a buffer, a tris buffer or a phosphate buffer may be used, which may further contain NaCl and serum albumin such as BSA. A buffer to be used herein may contain, in addition to them, a chelating agent such as EGTA (ethyleneglycol bis (2-aminoethylether) tetraacetic acid) or EDTA (ethylenediamine tetraacetic acid) or preservatives. Moreover, for efficient extraction, a buffer to be used herein may also contain a surfactant such as SDS or Tween20 and a reducing agent such as 2-ME or DTT. At this time, in the case of homogenized muscle tissue, 30 mL to 300 mL of a reagent for extraction may be added per gram of a homogenate. Also, in the case of freeze-dried powder, 200 mL to 2000 mL of a reagent for extraction may be added per gram of the powder. After extraction, centrifugation is carried out to recover a supernatant and then the thus obtained supernatant is used. Furthermore, as a reagent for allergen extraction, a commercially available reagent for extraction of a specific raw material (Morinaga Institute of Biological Science, Inc., FASPEK/Extraction Reagent For Specified Ingredient) may be used. At this time, in the case of homogenized muscle tissue, 5 mL to 50 mL, preferably 10 mL to 30 mL, further preferably 15 mL to 25 mL of a reagent for extraction of a specific raw material may be added per gram of a homogenate. Also, in the case of freeze-dried powder, 5 mL to 50 mL, preferably 10 mL to 30 mL, further preferably 15 mL to 25 mL of a reagent for extraction of a specific raw material may be added per 0.2 g of the powder. After extraction, centrifugation is carried out to recover a supernatant and then the thus obtained supernatant is used. The thus obtained supernatant may be mixed with sample dilution buffer, which is subjected to measurement of a specific protein to be measured. At this time, the total concentration of muscle tissue proteins contained in sample dilution buffer upon assay reaction ranges from 0.001% to 0.040% in any extraction method. Also, when a purified muscle tissue-derived protein is used instead of an unpurified muscle tissue-derived protein, the purified protein may be mixed with sample dilution buffer, which is subjected to measurement of a specific protein to be measured. For example, when purified tropomyosin is used, the protein is preferably added to sample dilution buffer, so that the total concentration ranges from 0.001% to 0.040%.

The present invention also encompasses, when a specific protein such as a food allergen protein that is a substance to be detected is measured by an immunoassay, a reagent composition for dilution and preparation of the specific protein, which contains the above muscle tissue-derived protein. The reagent composition is prepared on the basis of using a Tris buffer, a phosphate buffer, or the like, which may contain serum albumin such as BSA, a surfactant such as Tween20, NaCl, and a preservative, for example. Furthermore, the present invention further encompasses a kit comprising the above reagent composition for measuring by an immunoassay a specific protein such as a food allergen protein that is a substance to be detected. The kit may comprise an antibody against a specific protein that is a substance to be detected, a calibration standard, and the like. Such calibration standard to be used herein may be a purified product of a specific protein to be measured or a total protein extract from an animal as a raw material from which the specific protein is derived.

A specific protein to be measured may be measured by an immunoassay such as ELISA, RIA (radioimmunoassay), latex agglutination assay, or Western blotting. At this time, an antibody against a specific protein to be measured is used.

The measurement (assay) method of the present invention is performed as follows, for example.

Preparation of Sample Dilution Buffer

Probine (freeze-dried powder of Alaska pollack minced fish flesh: Maruha Nichiro Foods, Inc.) is added to a tris buffer (20 mM Tris/154 mM NaCl (pH 7.4) (TBS), 0.05% Tween20, 0.05% Proclin 200, 2.75 mM EDTA, pH 7.4) at approximately 2 g/L, and the mixture stirred for 15 hours at room temperature. The mixture is centrifuged at 3500 rpm for 30 minutes and then the supernatant is filtered. BSA (Bio-Rad) is added to the solution to approximately 1%, so that an sample dilution buffer (reagent composition for dilution and preparation) is prepared.

Preparation of Food Extract Containing Specific Protein that is a Substance to be Detected A 1 g of a food homogenized sample was added to 19 ml of extraction solution (Morinaga Institute of Biological Science, Inc., FASPEK/Extraction Reagent For Specified Ingredient) and the mixture was then shaken for 12 hours at room temperature for extraction. After the extraction, the sample was centrifuged at 3000×g for 20 min. and supernatant was filtered. The thus obtained filtrate is used as a food extract.

Measurement

The food extract diluted 20 times using sample dilution buffer and subjected to ELISA. If further dilution is required, dilution is performed using an sample dilution buffer prepared by adding a reagent for extraction reagent for specified ingredient to a sample dilution buffer in a 1:20 volume ratio and then the solution is subjected to measurement. When crustacean tropomyosin is a target for measurement, sandwich ELISA constructed with anti tropomyosin antibodies were used. Specifically, a capturing antibody is coated on a 96-well plate for ELISA or the like and then blocking is performed using BSA or the like. After wells are washed with an appropriate buffer, the diluted sample solution is added. After predetermined incubation, wells are washed and then an enzyme-labeled antibody for detection is added. After predetermined incubation, wells are washed and then a substrate (3,3',5,5'-tetramethylbenzidine or the like) is added. After predetermined incubation, absorbance is detected, so that the content of a target protein in the food is calculated based on a standard curve.

EXAMPLES

The present invention will be described specifically by examples as follows, but the present invention is not limited by these examples.

Example 1

Preparation of Model Processed Food and of ELISA Calibration Standard Solution (1) Preparation of Model Processed Food Various model processed food specimens containing black tiger prawn muscle were prepared by the following method.

(i) Fish Sausage

Minced fish flesh, which is a major raw material for fish sausage, was homogenized using a food cutter and then a flavoring material such as common salt was added. To 3 kg of the raw material, 44 mg or 220 mg of freeze-dried powder of black tiger prawn muscle was added. The mixture was stirred well, covered by fish sausage casings, and then heated for 15 minutes at 121° C.

(ii) Freeze-Dried Egg Soup (FD Egg Soup)

Egg (224 g) was added to a solution prepared by adding 11.2 g of potato starch dissolved in 10 g of water to 502 g of water heated at 95° C. Then the solution was kept at 95° C. To 864 g of a flavoring material solution to which salt had been added, 6 mg or 30 mg of freeze-dried powder of black tiger prawn muscle was added, followed by thorough stirring. The flavoring material solution was added to the beaten egg solution. The solution was stirred well and then cooled to room temperature. Ten g portions of the solution were dissolved in a plastic tray. After preliminary freezing at −80° C., freeze drying was performed for 18 hours. After completion of freeze drying, samples were individually vacuum sealed. When the weights after freeze drying were measured, the weight of the product which 6 mg of the black tiger prawn muscle powder had been added, was decreased to approximately 20% and the weight of the product which 30 mg of powder had been added, was decreased to approximately 25% of its former weight.

(iii) Chicken Balls

Chicken meat which is a major raw material of chicken balls, was homogenized using a food cutter and then a flavoring material such as salt was added. The black tiger prawn muscle freeze-dried powder (14.7 mg) was added to 1 kg of the raw material. The mixture was ground up and then the mixture was preserved at −20° C.

(2) Preparation of Model Processed Food Extract

Fish sausage, FD egg soup, and chicken balls prepared as model processed foods by the method of (1) above were homogenized with food processor. A 1 g portion of each model processed foods was extracted using 19 mL of the extraction solution. The mixture was shaken and mixed well, so that the solid content was dispersed evenly. The mixture was shaken horizontally (90 rpm to 100 rpm, with a shaking width of approximately 3 cm) overnight (12 hours at room temperature), and then centrifuged at 3000×g for 20 min. The supernatant was filtered with filter paper, so that a model processed food extract was prepared.

(3) Preparation of ELISA Calibration Standard Solutions

In view of health harm, not the level of an allergen in a raw material but rather the total protein level in the raw material contained in a processed food is generally thought to be important when the level inducing food allergies is considered. Therefore, the total protein level in a shrimp raw material was used as the calibration standard solution level.

A 0.1 g sample of freeze-dried black tiger muscle powder was added to 10 mM Na-Phosphate/154 mM NaCl (pH 7.4) (PBS) containing 0.5% SDS, 2% mercaptoethanol, 10 µL/mL protease inhibitor cocktail and 10 µL/mL 0.5 M EDTA (Pierce, Halt Inhibitor Cocktail Kit Cat. No. 78410). The mixture was then shaken (90 rpm to 100 rpm, with a shaking width of approximately 3 cm) for 15 hours at room temperature for extraction. After the extraction, the sample was centrifuged at 10000×g for 30 min. and supernatant was filtered through 0.8 µm microfilter paper (ADVANTEC, DISMIC-25cs Cat. No. 25CS080AN). The extract was then heated at 100° C. for 10 minutes to prepare an ELISA calibration standard solution. The total protein concentration in the ELISA calibration standard solution was analyzed using a 2-D Quant protein assay kit (Amersham Biosciences, Cat. No. 80-6483-56), so that the value of the ELISA calibration standard solution was determined (3.42 mg/mL).

(4) Measurement of Crustacean Protein Content in Model Processed Food

The amount of crustacean protein/1 g the black tiger prawn muscle powder was approximately 684 mg. Therefore, the total crustacean protein content extracted in the food extract of each model processed food above was as calculated as follows. The total protein content in the extract obtained via addition of 44 mg of the black tiger prawn muscle powder of fish sausage was 500 ng/mL (10 ppm in the food), the same in the extract obtained via addition of 6 mg of FD egg soup was 595 ng/mL (11.9 ppm in the food), the same in the extract obtained via addition of 14.7 mg of chicken ball powder was 500 ng/mL (10 ppm in the food), the same in the extract obtained via addition of 220 mg of fish sausage powder was 2500 ng/mL (50 ppm in the food), and the same in the extract obtained via addition of 30 mg of FD egg soup powder was also 2500 ng/mL (50 ppm in the food).

Example 2

Measurement Using Sample Dilution Buffer to which Minced Fish Fresh Extract (Containing Muscle Tissue Protein) was Added (1) Preparation of Sample Dilution Buffer (Minced Fish Fresh)

The minced fish flesh of Alaska Pollack (Maruha Nichiro Foods, Inc.) was homogenized using a mortar. A 1 g portion of the sample was extracted using 19 mL of the extraction solution. The mixture was shaken overnight (17 hours) at room temperature. After extraction, the extract was centrifuged at 3,000×g for 20 minutes and then the supernatant was filtered using filter paper to prepare a stock solution of the minced fish fresh extract. To this stock solution, an equivalent volume of extraction reagent for specified ingredient was added. The solution was diluted 20-fold using assay solution (1% BSA/ 0.05% Tween20/0.05% Proclin 200 (Supelco, Cat. No. 500380)/20 mM TBS, pH7.4) to prepare sample dilution buffer (minced fish fresh).

(2) Measurement Using Solution for Addition and Dilution of Minced Fish Fresh Extract The model processed foods prepared in Example 1 were measured. The measurement system was evaluated based on the percentages (recovery rates) of measured values with respect to the total crustacean protein content in the model processed foods and the dilution linearity of samples [regression coefficient ($R^2$)].

(i) Preparation of Calibration Standard Solution (Test Group)

The ELISA calibration standard solution in Example 1-(3) was diluted 3420-fold (1 µg/mL) using the solution of the minced fish fresh extract in (1) above and then further diluted 20-fold (50 ng/mL) using 1% BSA/0.05% Tween20/0.05% Proclin 200/20 mM TBS (pH 7.4). Moreover, the resultant was subjected to 2-fold serial dilution from 50 ng/mL to 0.78125 ng/mL using the sample dilution buffer. Thus, a calibration standard solution test product containing the Alaska pollack minced fish fresh extract was prepared.

(Control Group)

The ELISA calibration standard solution in Example 1-(3) was diluted 3420-fold using the reagent for extraction of a specific raw material and then further diluted (50 ng/mL) 20-fold using 1% BSA/0.05% Tween20/0.05% Proclin 200/ 20 mM TBS (pH 7.4). Moreover, the resultant was subjected to 2-fold serial dilution from 50 ng/mL to 0.78125 ng/mL using 1% BSA/0.05% Tween20/0.05% Proclin 200/20 mM TBS (pH 7.4) containing 1/20 v/v of extraction reagent for specified ingredient. Thus, a control calibration standard solution containing no Alaska pollack minced fish fresh extract was prepared.

(ii) Preparation of Diluted Solution of Model Processed Food Extract
(Test Group)

A model processed food extract prepared in Example 1-(2) and the stock solution of the minced fish fresh extract of (1) above were mixed in equivalent volumes (2-fold diluted solution). The solution was further diluted 20-fold (40-fold diluted solution) using 1% BSA/0.05% Tween20/0.05% Proclin 200/20 mM TBS (pH 7.4). Furthermore, the 40-fold diluted solution as a stock solution was subjected to 2-fold serial dilution up to 1/32 (1280-fold) using the sample dilution buffer (minced fish fresh) of (1) above. Thus, the diluted test solution of each model processed food extract containing the Alaska Pollack minced fish fresh extract was prepared.
(Control Group)

The model processed food extract prepared in Example 1-(2) and extraction reagent for specified ingredient were mixed in equivalent volumes (2-fold diluted solution) and then the solution was diluted 20-fold (40-fold diluted solution) using 1% BSA/0.05% Tween20/0.05% Proclin 200/20 mM TBS (pH 7.4). Moreover, the 40-fold diluted solution as a stock solution was subjected to 2-fold serial dilution up to 1/32 (1280-fold) using 1% BSA/0.05% Tween20/0.05% Proclin 200/20 mM TBS (pH7.4) containing 1/20 v/v of extraction reagent for specified ingredient. Thus, a diluted control solution of the model processed food extract containing no Alaska pollack minced fish fresh extract was prepared.

(iii) Measurement

A capturing antibody against black tiger tropomyosin was coated on a 96-well microtiter plate or the like. Subsequently, the plates were blocked with BSA or the like. Blocking solutions were removed and then the test calibration standard solution (50 ng/mL to 0.78125 ng/mL), the control calibration standard solution (50 ng/mL to 0.78125 ng/mL), the diluted test solution of model processed food extract (40-fold to 1280-fold) and the diluted control solution of the model processed food extract (40-fold to 1280-fold) were added (100 μL/well). After 1 hour of incubation at 25° C., wells were washed and then 100 μL of a detection antibody against black tiger tropomyosin, which had been conjugated with horseradish peroxidase (HRP), was added. After 1 hour of incubation at 25° C., wells were washed and then 100 μL of a substrate (3,3', 5,5'-tetramethylbenzidine) was added. After 20 minutes of incubation at 25° C., the reaction was stopped by the addition of 0.1 N sulfuric acid (100 μL/well). Absorbance of each well was measured using a plate reader at 450 nm with 600 nm to 650 nm as the calibration wavelength.

A standard curve was produced based on the results of the test calibration standards and the control calibration standards. Based on the standard curve, the protein concentrations of the diluted test solution of the model processed food extract (40-fold to 1280-fold) and the diluted control solution of the model processed food extract (40-fold to 1280-fold) were each calculated.

(iv) Results

Figure 1B:
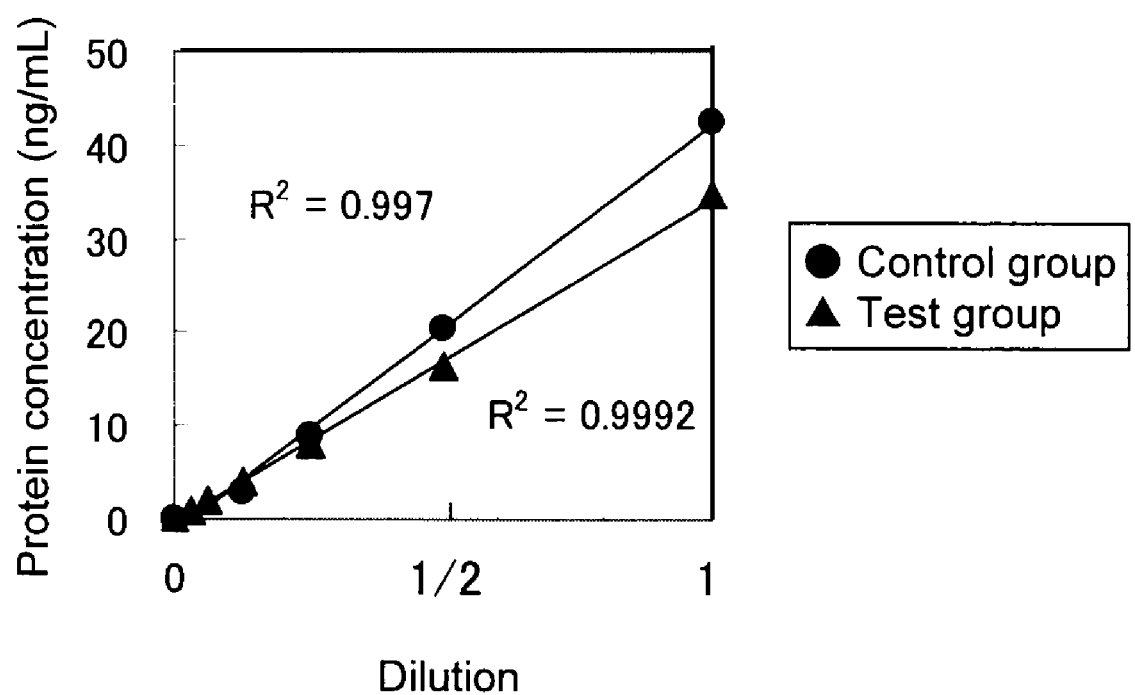
FIG. 1B shows the relationship between dilution rates and measured values when an extract of an FD egg soup specimen was subjected to 2-fold serial dilution in a test using an extract of Alaska pollack minced fish fresh as a muscle tissue-derived protein.

FIG. 1 and Table 1 show the results of measuring fish sausage (50 ppm) and FD egg soup (50 ppm).

TABLE 1

Recovery rate of fish sausage and FD egg soup

|  | Test group | Control group |
| --- | --- | --- |
| Fish sausage | 64.9% to 69.1% | 152.4% to 466.0% |
| FD egg soup | 50.8% to 55.4% | 37.5% to 68.1% |

When the solution prepared without the addition of Alaska pollack minced fish fresh extract had been used as sample dilution buffer (control group) (● in FIG. 1A to FIG. 1B and Table 1), the recovery rate of the fish sausage ranged from 152.4% to 466.0% and the regression coefficient was $R^2=0.9374$. The recovery rate of the FD egg soup ranged from 37.5% to 68.1% and the regression coefficient was $R^2=0.997$.

Meanwhile, when the solution prepared by adding the Alaska pollack minced fish fresh extract had been used as assay solution (test group) (▲ in FIG. 1A to FIG. 1B and Table 1), the recovery rate of the fish sausage ranged from 64.9% to 69.1% and the regression coefficient was $R^2=0.9999$. Furthermore, the recovery rate of the FD egg soup ranged from 50.8% to 55.4% and the regression coefficient was $R^2=0.9992$. Thus, recovery rates and dilution linearity were improved in all model processed foods. Therefore, it was revealed that correct measurement is possible in the test groups without food matrix effects.

Example 3

Test 1 Addition of the Extract of Minced Fish Fresh Dry Powder (Probine)

(1) Preparation of Sample Dilution Buffer (Probine) 1

A 0.2 g portion of Probine (freeze dried powder of Alaska Pollack minced fish fresh: Maruha Nichiro Foods, Inc.) was extracted using 19.8 mL of extraction reagent for specified ingredient. The mixture was shaken overnight (17 hours) at room temperature. After extraction, the extract was centrifuged at 3,000×g for 20 minutes and then the supernatant was filtered using filter paper. The solution diluted 20-fold using assay solution (1% BSA/0.05% Tween20/0.05% Proclin 200 (Supelco, Cat. No. 500380)/20 mM TBS, pH7.4) so that sample dilution buffer (Probine) 1 was prepared.

(2) Measurement Using Solution for Addition and Dilution of Probine Extract (i) Preparation of Calibration Standard Solution The ELISA calibration standard solution prepared according to the method of Example 1 was diluted 3420-fold (1 μg/mL) using the stock solution of the Probine extract in (1) above and then further diluted 20-fold (50 ng/mL) using 1% BSA/0.05% Tween20/0.05% Proclin 200/20 mM TBS (pH 7.4). Moreover, the resultant was subjected to 2-fold serial dilution from 50 ng/mL to 0.78125 ng/mL using sample dilution buffer (Probine) 1. Thus, a test calibration standard solution containing the Probine extract was prepared.

(ii) Preparation of Diluted Solution of Model Processed Food Extract

A model processed food extract (fish sausage or FD egg soup) prepared by the method according to Example 1 and the stock solution of Probine extracts were mixed in equivalent volumes (2-fold diluted solution). The solution was further diluted 20-fold (40-fold diluted solution) using 1% BSA/0.05% Tween20/0.05% Proclin 200/20 mM TBS (pH 7.4). Furthermore, the 40-fold diluted solution as a stock solution was subjected to 2-fold serial dilution up to 1/32 (1280-fold) using the sample dilution buffer (Probine) 1. Thus, diluted test solutions of the model processed food extracts containing the Probine extract were prepared.

A control group similar to that in Example 2 was prepared.
Measurement was performed by the same method as that in Example 2.

(iii) Results

Figure 2A:
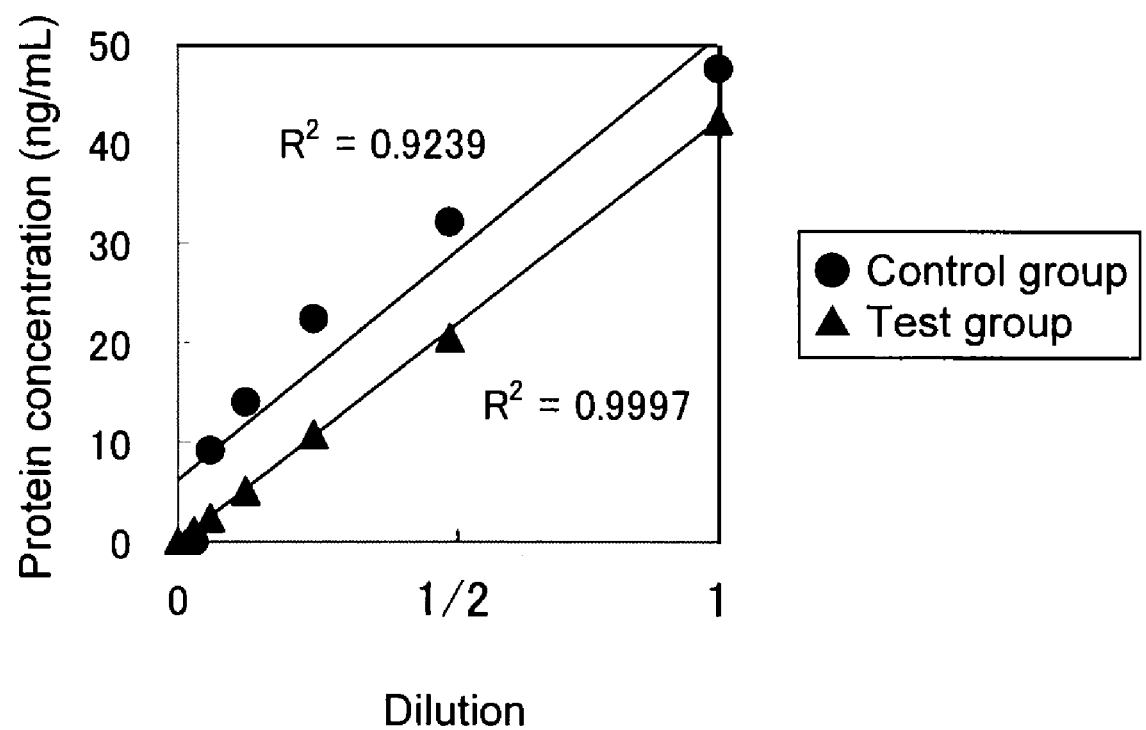
FIG. 2A shows the relationship between dilution rates and measured values when an extract of a fish sausage specimen was subjected to 2-fold serial dilution in a test using an extract of dry powder of Alaska Pollack minced fish fresh as a muscle tissue-derived protein.
Figure 2B:
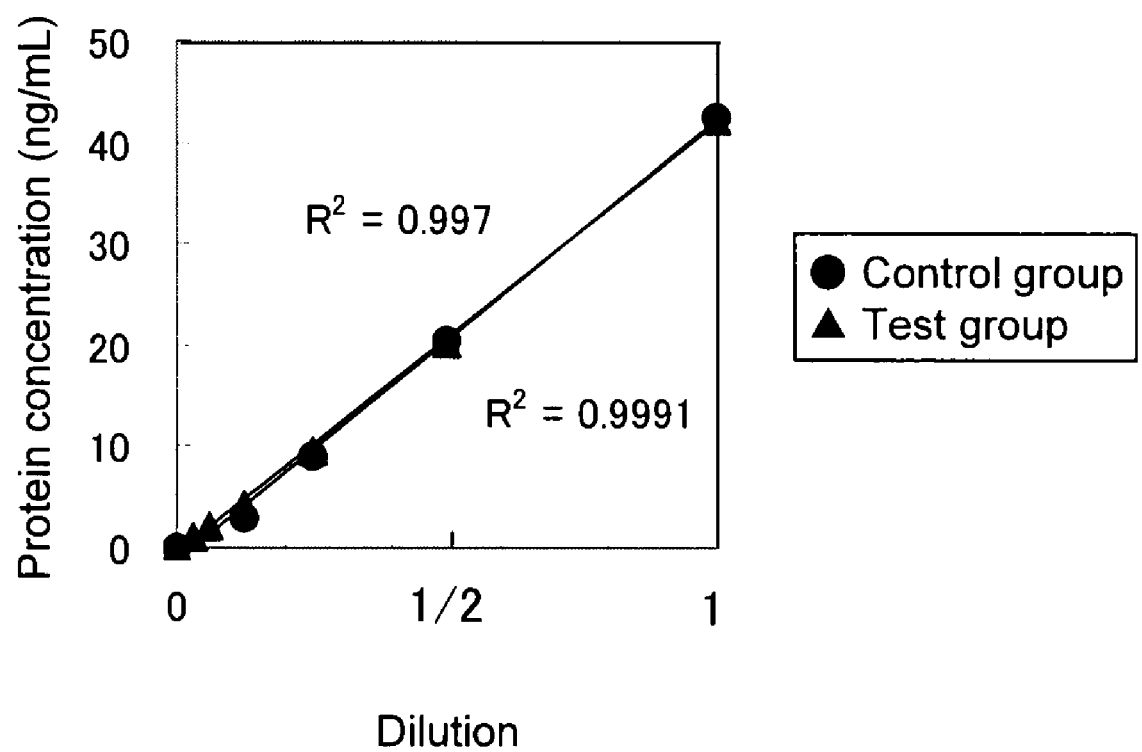
FIG. 2B shows the relationship between dilution rates and measured values when an extract of an FD egg soup specimen was subjected to 2-fold serial dilution in a test using an extract of dry powder of Alaska pollack minced fish fresh as a muscle tissue-derived protein.

FIG. 2 and Table 2 show the results of measuring fish sausage (50 ppm) and FD egg soup (50 ppm).

TABLE 2

Recovery rates of fish sausage and FD egg soup

|  | Test group | Control group |
|---|---|---|
| Fish sausage | 62.1% to 68.1% | 152.4% to 466.0% |
| FD egg soup | 55.6% to 67.7% | 37.5% to 68.1% |

When the solution prepared without the addition of Probine extract to sample dilution buffer was used (control group) (● in FIG. 2A to FIG. 2B and Table 2), the recovery rate of the fish sausage ranged from 152.4% to 466.0% and the regression coefficient was $R^2=0.9239$. The recovery rate of the FD egg soup ranged from 37.5% to 68.1% and the regression coefficient was $R^2=0.997$.

Meanwhile, when the solution prepared by adding the Probine extract to sample dilution buffer was used (test group) (▲ in FIG. 2A to FIG. 2B and Table 2), the recovery rate of the fish sausage ranged from 62.1% to 68.1% and the regression coefficient was $R^2=0.9997$. Furthermore, the recovery rate of the FD egg soup ranged from 55.6% to 67.7% and the regression coefficient was $R^2=0.9991$. Thus, recovery rates and dilution linearity were improved in all model processed foods. Therefore, it was revealed that correct measurement is possible in test groups without food matrix effects.

Example 4

Test 2 Addition of Extract of Minced Fish Fresh Dry Powder (Probine)

(1) Preparation of Assay Solution (Probine) 2

A 2.3 g/L of Probine was added to a tris buffer (20 mM Tris/154 mM NaCl (pH 7.4) (TBS), 0.05% Tween20, 0.05% Proclin 200, 2.75 mM EDTA, pH 7.4), The mixture was stirred with a stirrer at room temperature for 15 hours. The thus obtained extract was centrifuged at 9,110×g for 30 minutes. The supernatant was filtered with a 0.22 μm filter (Corning, 500 mL Bottle Top Filter, 22 μm PES, Cat. No. 431118) and then BSA was added to the solution to 1%, thereby preparing sample dilution buffer (Probine) 2 (test group).

Moreover, 1% BSA/0.05% Tween20/0.05% Proclin 200/20 mM TBS (pH 7.4) was used as a control assay solution (control group).

(2) Measurement
(i) Preparation of Calibration Standard Solution

The ELISA calibration standard solution prepared according to the method of Example 1 was diluted 3420-fold to 1 μg/mL using a reagent for extraction reagent for specified ingredient, thereby preparing a calibration standard solution.

The calibration standard solution was diluted 20-fold with the sample dilution buffer (Probine) 2 or the sample dilution buffer (control). Moreover, the resultant was subjected to 2-fold serial dilution from 50 ng/mL to 0.78125 ng/mL using the sample dilution buffer (Probine) 2 or the sample dilution buffer (control) containing 1/20 v/v of extraction reagent for specified ingredient. Thus, a test calibration standard solution was prepared.

(ii) Preparation of Diluted Solution of Model Processed Food Extract

A model processed food extract prepared by the method according to Example 1 was diluted 20-fold (20-fold diluted solution) using the sample dilution buffer (Probine) 2 or the sample dilution buffer (control). Furthermore, the 20-fold diluted solution of the test group was subjected to 2-fold serial dilution to 1/16 and the same of the control group was subjected to 2-fold serial dilution to 1/32 using the sample dilution buffer (Probine) 2 or the sample dilution buffer (control) containing 1/20 v/v of extraction reagent for specified ingredient.

Measurement was performed by the same method as that in Example 2.

(3) Results

Figure 3A:
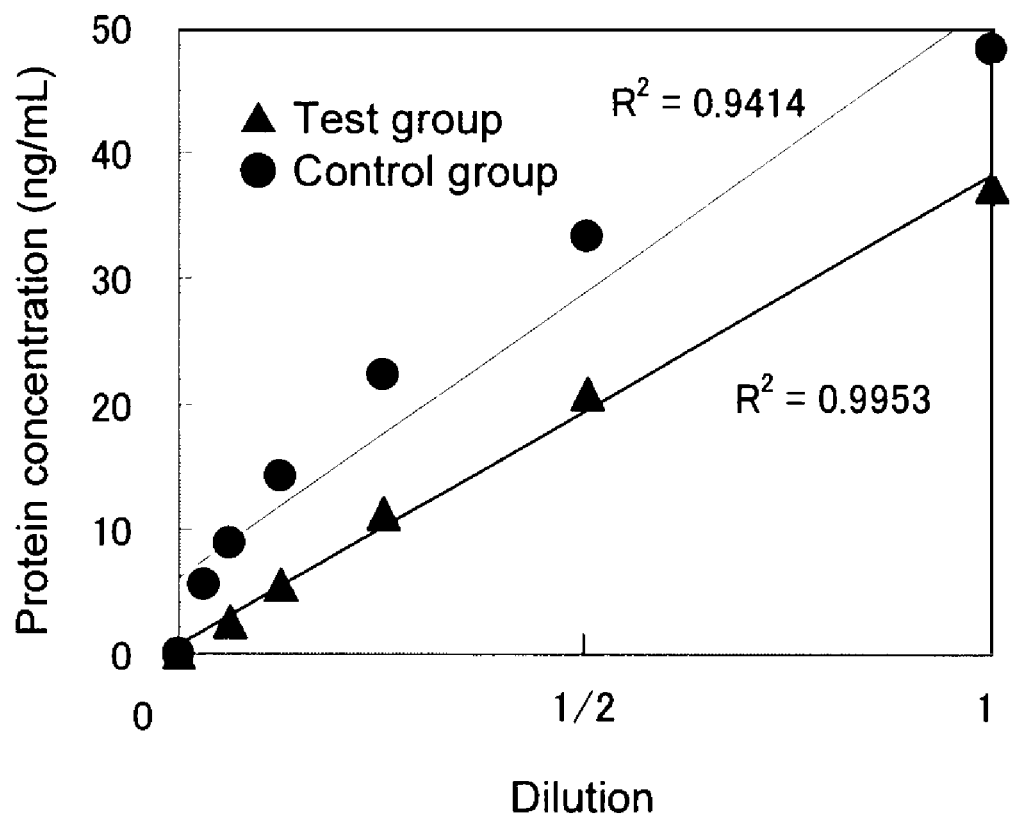
FIG. 3A shows the relationship between dilution rates and measured values when an extract of a fish sausage specimen was subjected to 2-fold serial dilution in a test using an extract of dry powder of Alaska Pollack minced fish fresh as a muscle tissue-derived protein.
Figure 3B:
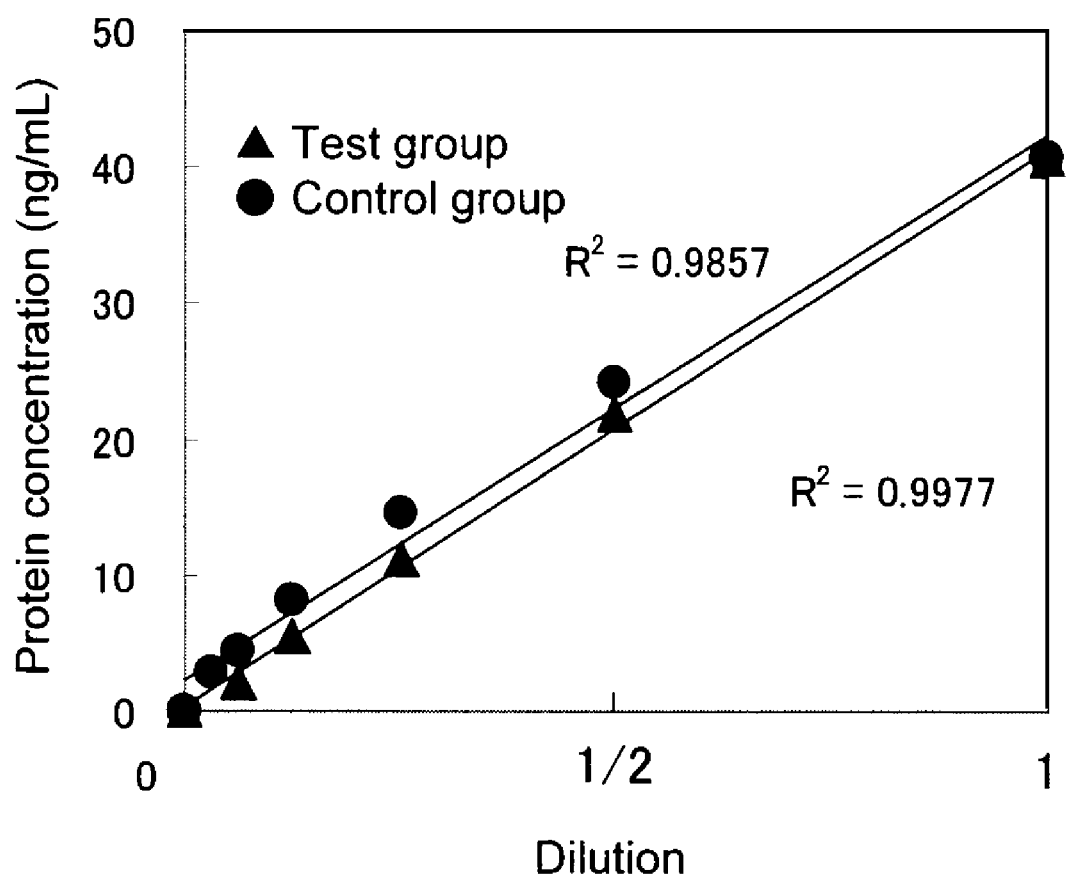
FIG. 3B shows the relationship between dilution rates and measured values when an extract of an FD egg soup specimen was subjected to 2-fold serial dilution in a test using an extract of dry powder of Alaska pollack minced fish fresh as a muscle tissue-derived protein.
Figure 3C:
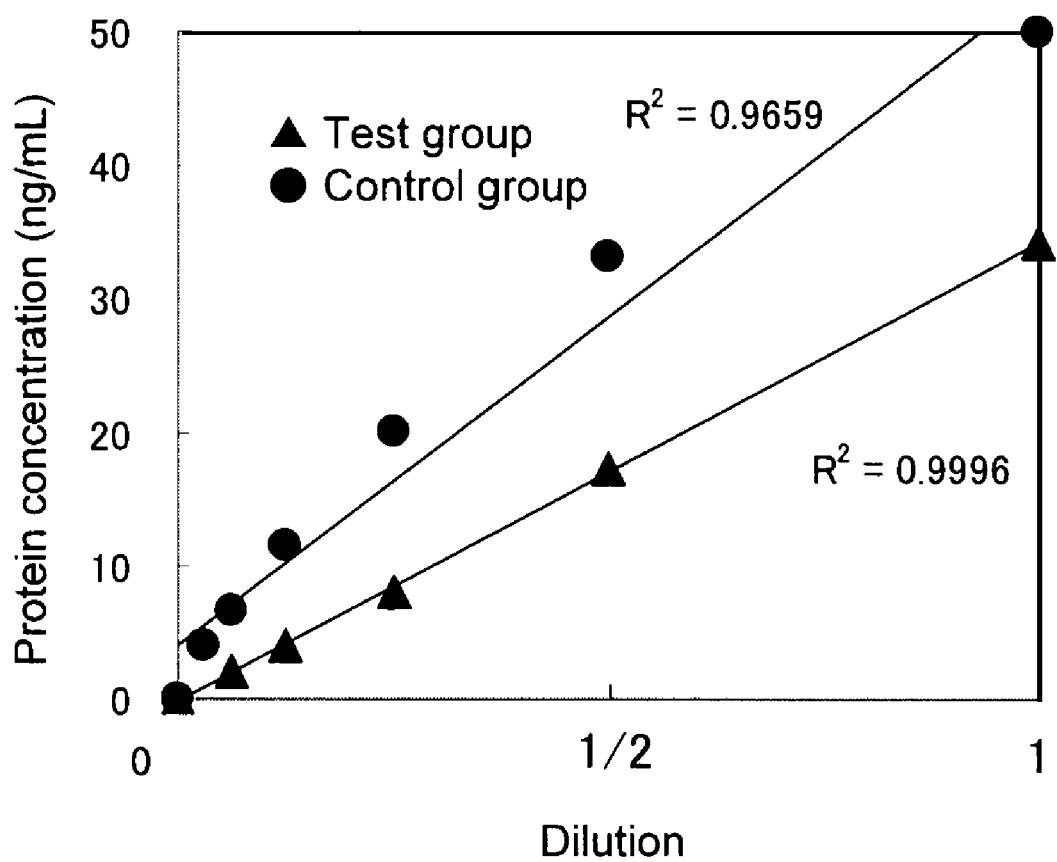
FIG. 3C shows the relationship between dilution rates and measured values when an extract of a chicken ball specimen was subjected to 2-fold serial dilution in a test using an extract of dry powder of Alaska pollack minced fish fresh as a muscle tissue-derived protein.

FIGS. 3A to 3C show the dilution curves for fish sausage (10 ppm), FD egg soup (11.9 ppm), and chicken balls (10 ppm) when the sample dilution buffer (control) was used (control group) or when the sample dilution buffer (Probine) 2 was used (test group) for measurement.

Furthermore, Table 3 shows the recovery rate of each model processed food above.

TABLE 3

Recovery rates of fish sausage, FD egg soup, and chicken balls

|  | Test group | Control group |
|---|---|---|
| Fish sausage | 108.2% to 130.7% | 139.3% to 405.0% |
| FD egg soup | 94.4% to 124.6% | 112.5% to 196.5% |
| Chicken balls | 101.2% to 109.0% | 157.0% to 333.7% |

When the sample dilution buffer (control) was used (control group) (● in FIG. 3A to FIG. 3C and Table 3), the recovery rate of the fish sausage ranged from 139.3% to 405.0% and the regression coefficient was $R^2=0.9414$. The recovery rate of the FD egg soup ranged from 112.5% to 196.5% and the regression coefficient was $R^2=0.9857$. The recovery rate of the chicken balls ranged from 157.0% to 333.7% and the regression coefficient was $R^2=0.9659$. It could not be easily said that these values had been measured correctly.

Meanwhile, when the sample dilution buffer (Probine) 2 had been used (test group) (▲ in FIG. 3A to FIG. 3C and Table 3), the recovery rate of the fish sausage ranged from 108.2% to 130.7% and the regression coefficient was $R^2=0.9953$. Furthermore, the recovery rate of the FD egg soup ranged from 94.4% to 124.6% and the regression coefficient was $R^2=0.9977$. The recovery rate of the chicken balls ranged from 101.2% to 109.0% and the regression coefficient was $R^2=0.9996$. Thus, in all the model processed foods, very good recovery rates and dilution linearity were observed when the sample dilution buffer (Probine) 2 had been used. Moreover, recovery rates more improved than those in Example 3 were observed.

Example 5

Test 3 Addition of Extract of Minced Fish Fresh Dry Powder (Probine)

(1) Preparation of Sample Dilution Buffer (Probine) 3

A 10 g/L of Probine was added to a buffer (prepared by mixing 100 mM Tris/0.77 M NaCl (pH 7.4) (5×TBS) with 0.25% Tween20, 0.25% Proclin 200). The mixture was stirred with a stirrer at room temperature for 15 hours. The thus obtained extract was diluted 5-fold with distilled water and then 0.5 M EDTA (pH 7.4) was added to a final concentration of 2.5 mM. Subsequently, the resultant was centrifuged at 9,110×g for 30 minutes. The supernatant was filtered with a 0.22 μm filter and then BSA was added to the solution to 1%, thereby preparing sample dilution buffer (Probine) 3 (test group).

Moreover, 1% BSA/0.05% Tween20/0.05% Proclin 200/20 mM TBS (pH 7.4) was used as a control sample dilution buffer (control group).

(2) Measurement
(i) Preparation of Calibration Standard Solution

The ELISA calibration standard solution prepared by the method according to Example 1 was diluted 3420-fold to 1 μg/mL using a reagent for extraction of a specific raw material, thereby preparing a calibration standard solution.

The calibration standard solution was diluted 20-fold with the sample dilution buffer (Probine) 3 or the sample dilution buffer (control). Moreover, the resultant was subjected to 2-fold serial dilution to 0.78125 ng/mL using the sample dilution buffer (Probine) 3 or the sample dilution buffer (control) containing 1/20 v/v of extraction reagent for specified ingredient.

(ii) Preparation of Diluted Solution of Model Processed Food Extract

The model processed food extract prepared by the method according to Example 1 was diluted 20-fold using the sample dilution buffer (Probine) 3 or the sample dilution buffer (control). The resultant was subjected to measurement. The 20-fold diluted solution was further diluted 5-fold (100-fold dilution) using the sample dilution buffer (Probine) 3 or the sample dilution buffer (control) containing 1/20 v/v of extraction reagent for specified ingredient. The resultant was also subjected to measurement.

Measurement was performed by the same method as that in Example 2.

(3) Results

Table 4 shows the recovery rates of the fish sausage (10 ppm), the FD egg soup (11.9 ppm), and the chicken balls (10 ppm) diluted 20-fold or diluted 100-fold using the control sample dilution buffer (control group) or the sample dilution buffer (Probine) 3 (test group) in the measurement. When the sample dilution buffer (control) had been used, the recovery rate of the fish sausage diluted 20-fold was 139.7%; however, the same rate for the fish sausage diluted 100-fold was 258.0%. The recovery rate of the FD egg soup diluted 20-fold was 112.5% and the same rate for the FD egg soup diluted 100-fold was 161.6%. The recovery rate of the chicken balls diluted 20-fold was 157.0% and the same rate for the chicken balls diluted 100-fold was 252.5%. In all the model processed foods, it cannot be easily said that correct measurement could be performed, because the food matrix could affect the recovery rate and the dilution linearity in control group. Meanwhile, the results obtained via the use of the sample dilution buffer (Probine) 3 are as follows. The recovery rate of the fish sausage diluted 20-fold was 100.3%; however, the same rate for the fish sausage diluted 100-fold was 116.6%. The recovery rate of the FD egg soup diluted 20-fold was 106.5% and the same rate for the FD egg soup diluted 100-fold was 109.7%. The recovery rate of the chicken balls diluted 20-fold was 97.4% and the same rate for the chicken balls diluted 100-fold was 96.2%. It was revealed that the use of the sample dilution buffer (Probine) 3 resulted in very good recovery rates and dilution linearity in all the model processed foods without food matrix effects.

TABLE 4

Recovery rates of fish sausage, FD egg soup, and chicken balls

| | | Test group | Control group |
|---|---|---|---|
| Fish sausage | 20-fold dilution | 100.3% | 139.7% |
| | 100-fold dilution | 116.6% | 258.0% |
| FD egg soup | 20-fold dilution | 106.5% | 112.5% |
| | 100-fold dilution | 109.7% | 161.6% |
| Chicken balls | 20-fold dilution | 97.4% | 157.0% |
| | 100-fold dilution | 96.2% | 252.5% |

Example 6

Verification of Protein Concentration in Sample Dilution Buffer

Protein concentrations in sample dilution buffer were varied and then model processed foods were subjected to measurement. The resulting recovery rates were then examined.

(1) Preparation of Various Sample Dilution Buffers

Sample dilution buffer (minced fish fresh) and sample dilution buffer (Probine) 1 were prepared according to the methods described in Examples 2 and 3. Sample dilution buffers (Probine) at various concentrations (0.5, 1, 2.3, 2.5, 3, and 5 g/L) were prepared according to the method described in Example 4-(1). Protein concentrations in the sample dilution buffer to which the minced fish fresh and Probine had been added were measured before addition of BSA.

(2) Measurement

The model processed foods prepared in Example 1, the fish sausage (50 ppm) and the FD egg soup (50 ppm), were measured using the sample dilution buffer (minced fish fresh) and the sample dilution buffer (Probine) 1 prepared in (1) (20-fold dilution only; see Examples 2 to 5). Also, the model processed foods prepared in Example 1, the fish sausage (10 ppm) and the FD egg soup (11.9 ppm), were measured using various sample dilution buffer (Probine). Measurement was performed by the same method as that in Example 2.

(3) Results

Table 5 shows the recovery rates of the model processed foods (the fish sausage and the FD egg soup) when the sample dilution buffer (minced fish fresh) and the sample dilution buffer (Probine) 1 were used. Table 6 shows the recovery rates of the model processed foods (the fish sausage and the FD egg soup) when various sample dilution buffers (Probine) were used. Table 5 and Table 6 also show the protein concentration of each sample dilution buffer.

TABLE 5

Recovery rates of model processed foods when the sample dilution buffer (minced fish fresh) and the sample dilution buffer (Probine) 1 were used

| | | Sample dilution buffer (minced fish fresh) | Sample dilution buffer (Probine) 1 |
|---|---|---|---|
| Protein concentration (µg/mL) | | 156 | 247 |
| Recovery rate (%) | Fish sausage | 69 | 68 |
| | FD egg soup | 55 | 68 |

TABLE 6

Recovery rates of model processed foods when various sample dilution buffers (Probine) were used

| | | 0.05% | 0.10% | 0.23% | 0.25% | 0.30% | 0.50% |
|---|---|---|---|---|---|---|---|
| Protein concentration (µg/mL) | | 100 | 130 | 263 | 279 | 313 | 730 |
| Recovery rate (%) | Fish sausage | 75 | 75 | 129 | 90 | 80 | 73 |
| | FD egg soup | 97 | 94 | 118 | 66 | 66 | 79 |

As shown in Table 5 and Table 6, when the protein concentration in sample dilution buffer (Probine) ranged from 100 µg/mL to 730 µg/mL, the recovery rate of a model processed food ranged from 55% to 129%. It was revealed that within the protein concentration range, good recovery rates could be obtained.

Example 7

Examination with the Use of Purified Tropomyosin (1) Preparation of Purified Tropomyosin As Crustacean tropomyosin, mammalian tropomyosin having low amino acid sequence homology was prepared from swine muscle tissue. Tropomyosin derived from the porcine skeletal muscle was obtained using the purification procedure of Greaser et al., (The Journal of Biological Chemistry Vol. 246, No. 13, 4226-4233, 1971). Porcine muscle tissue was homogenized using a blender and then the resultant was subjected to delipidization using acetone. The dried powder was extracted overnight with 1M KCl. The porcine tropomyosin was purified to apparent homogeneity by a three-step procedure: ammonium sulfate precipitation, isoelectric point precipitation and gel filtration chromatography on Superdex® 200 pg column. Fractions containing tropomyosin were collected and then dialysis was performed against 20 mM TBS (pH 7.4), so that purified tropomyosin was prepared.

(2) Preparation of Sample Dilution Buffer (Tropomyosin)

The purified tropomyosin was diluted to a predetermined concentration with 20 mM TBS (pH 7.4), BSA was added to a final concentration of 1%, and then Tweene® 20 and Proclin® 200 were added to a final concentration of 0.05%. The thus obtained solution was used as sample dilution buffer (tropomyosin).

(3) Measurement (i) Preparation of Calibration Standard Solution

The ELISA calibration standard solution prepared by the method according to Example 1 was diluted 3420-fold to 1 µg/mL using an extraction reagent for specified ingredient, The calibration standard solution was diluted 20-fold with the sample dilution buffer (tropomyosin) and then the resultant was subjected to 2-fold serial dilution to 0.78125 ng/mL using the sample dilution buffer (tropomyosin) containing 1/20 v/v of extraction reagent for specified ingredient.

(ii) Preparation of Diluted Solution of Model Processed Food Extract

A model processed food extract prepared by the method according to Example 1 was diluted 20-fold using sample dilution buffer (tropomyosin). Furthermore, the resultant was subjected to 2-fold serial dilution to 1/16 using sample dilution buffer (tropomyosin) containing 1/20 v/v of extraction reagent for specified ingredient.

Measurement was performed by the same method as that in Example 2. The measurement system was evaluated based on the percentages of measured values (recovery rates) with respect to the total crustacean protein content in model processed foods and dilution linearity of samples [regression coefficient ($R^2$)] were evaluated.

(4) Results

Figure 4:
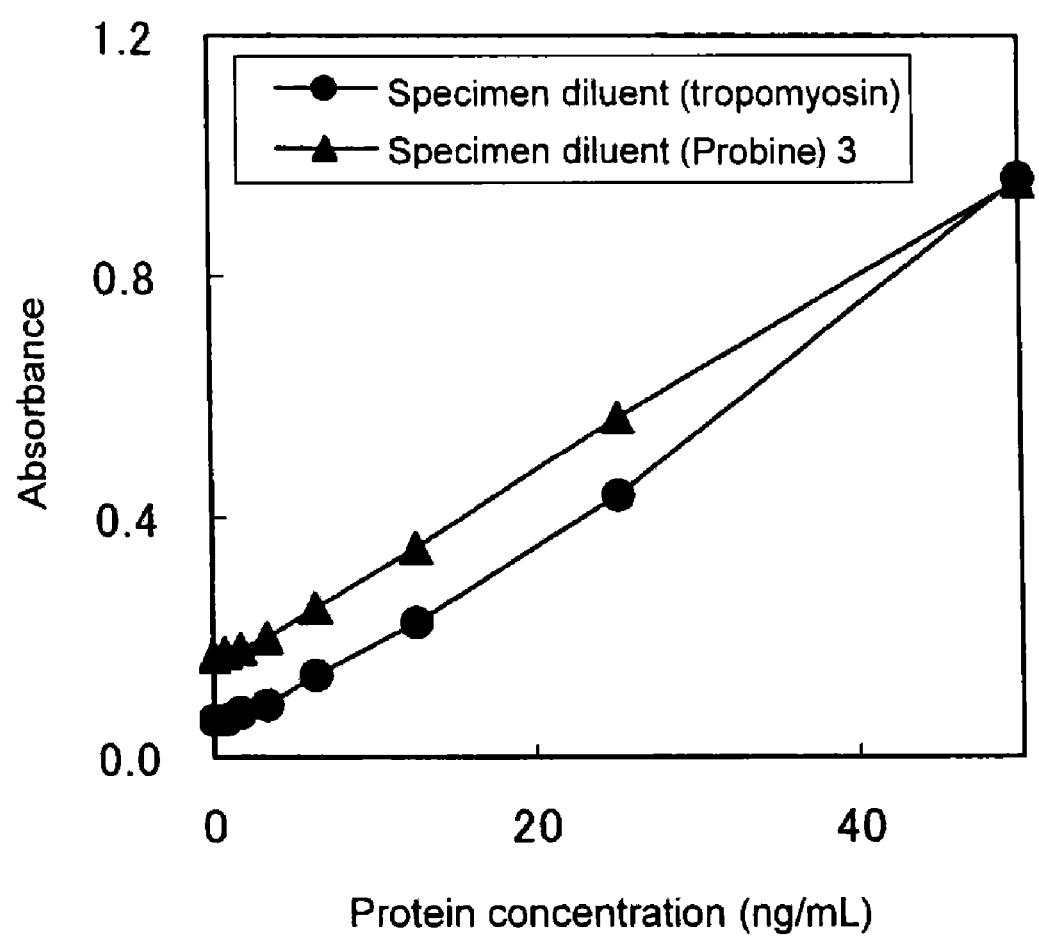
FIG. 4 shows the standard curve when measurement was carried out using sample dilution buffer (tropomyosin) of a specimen containing 0.02% tropomyosin or sample dilution buffer (Probine) 3.

FIG. 4 shows standard curves produced when measurement was performed using sample dilution buffer (tropomyosin) containing 0.02% tropomyosin or the sample dilution buffer (Probine) 3 described in Example 5. The absorbance at the protein concentration of 50 ng/mL was almost the same when any sample dilution buffer was used. However, whereas the background (absorbance at a protein concentration of 0 ng/mL) was high (0.17) in the case of using the sample dilution buffer (Probine) 3, the background was low (0.06) in the case of using the sample dilution buffer (tropomyosin).

Figure 5A:
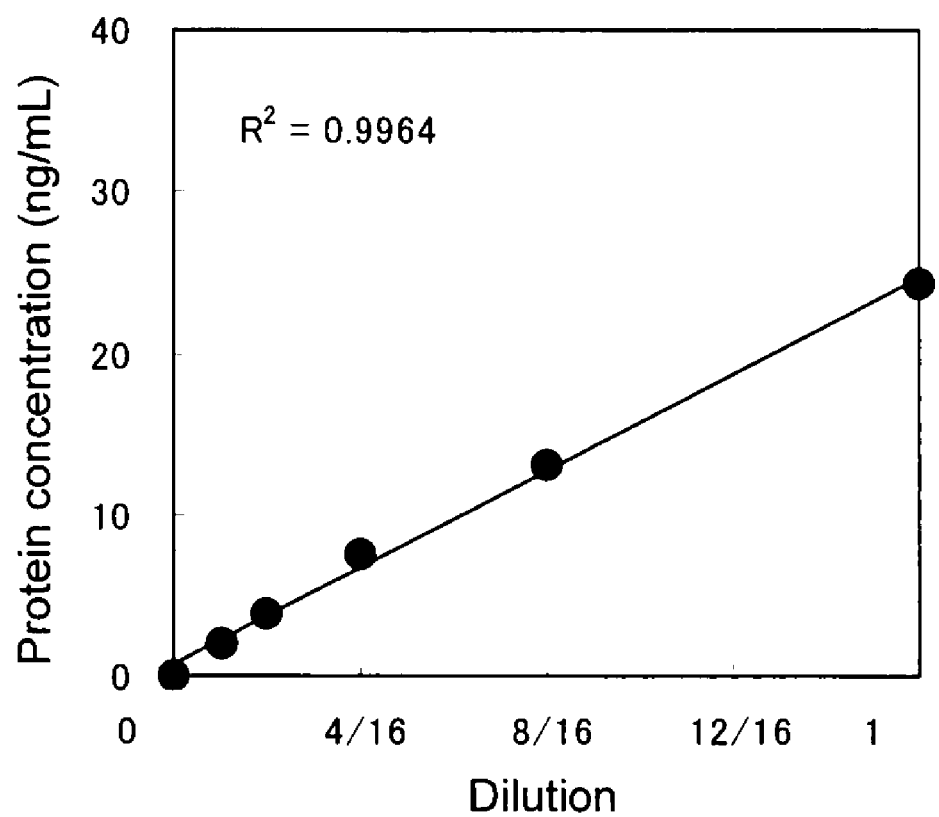
FIG. 5A shows the relationship between dilution rates and measured values when an extract of a fish sausage specimen was subjected to 2-fold serial dilution in a test using purified tropomyosin as a muscle tissue-derived protein.
Figure 5B:
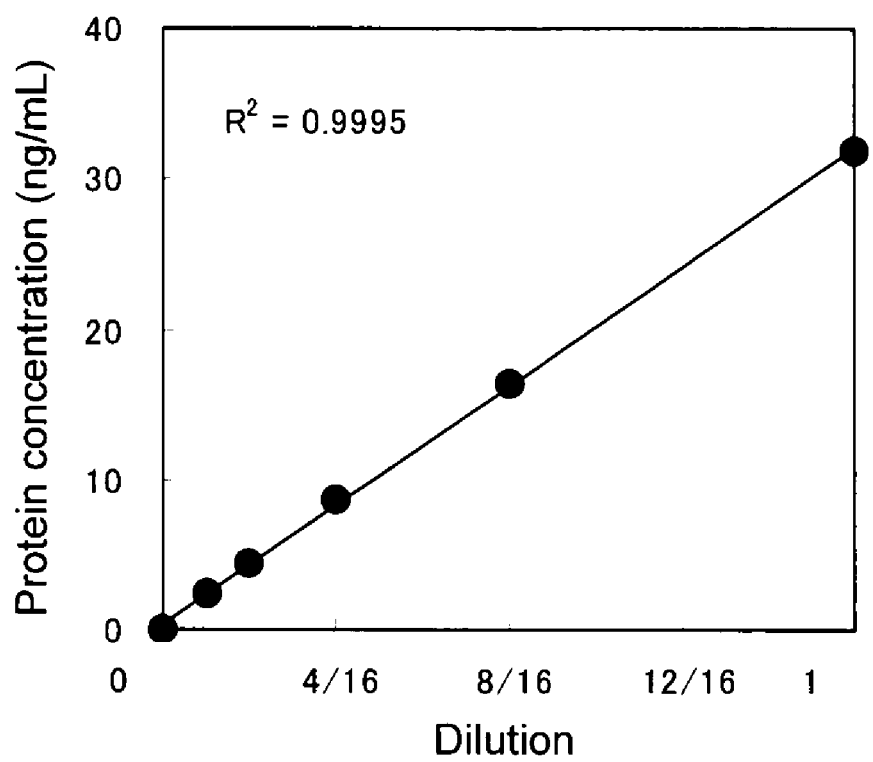
FIG. 5B shows the relationship between dilution rates and measured values when an extract of an FD egg soup specimen was subjected to 2-fold serial dilution in a test using purified tropomyosin as a muscle tissue-derived protein.
Figure 5C:
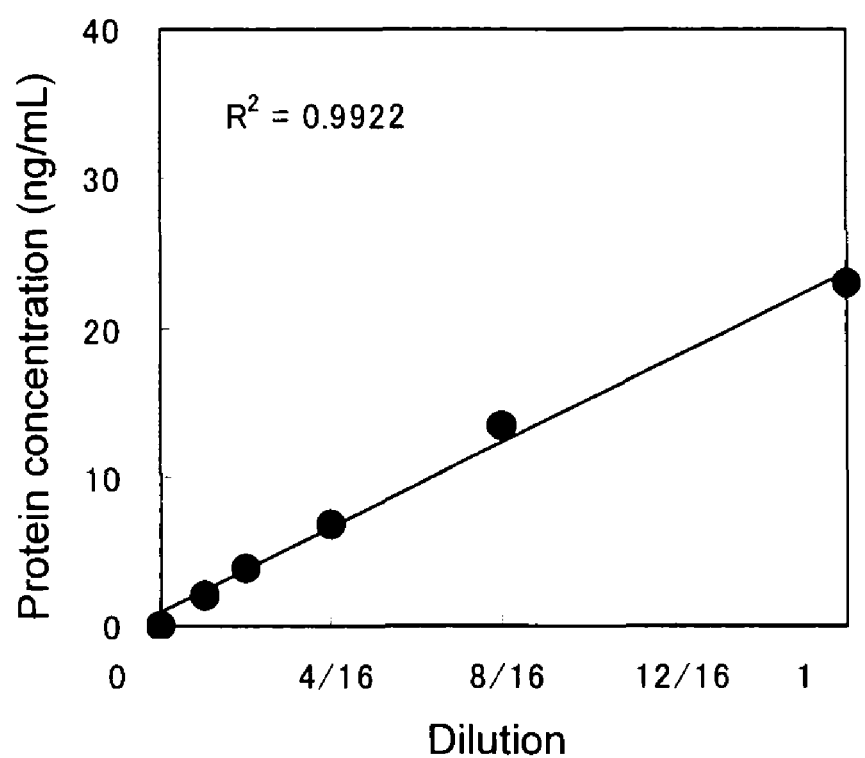
FIG. 5C shows the relationship between dilution rates and measured values when an extract of a chicken ball specimen was subjected to 2-fold serial dilution in a test using a purified tropomyosin as a muscle tissue-derived protein.

Subsequently, FIGS. 5A to 5C show the dilution curves for the fish sausage (10 ppm), the FD egg soup (11.9 ppm), and the chicken balls (10 ppm) using sample dilution buffer (tropomyosin) containing 0.02% tropomyosin was used.

The recovery rate of the fish sausage ranged from 97.3% to 132.6% and the regression coefficient of the dilution curve was $R^2$=0.9964. The recovery rate of the FD egg soup ranged from 107.3% to 124.2% and the regression coefficient of the dilution curve was $R^2$=0.9995. The recovery rate of the chicken balls ranged from 92.0% to 132.5% and the regression coefficient of the dilution curve was $R^2$=0.9922. Good recovery rates and dilution linearity were obtained in all the model processed foods. It was revealed that correct measurement could be performed by the use of the sample dilution buffer (tropomyosin) without food matrix effects.

Consequently, it was revealed that background reduction is possible using an sample dilution buffer with purified tropomyosin instead of an unpurified muscle tissue-derived protein such as Probine, while keeping good recovery rates and dilution linearity at levels similar to those in the case of using sample dilution buffer with unpurified muscle tissue-derived protein has been added.

Example 8

Examination of Concentrations of Purified Tropomyosin Added

The recovery rates and dilution linearity obtained upon measurement of model processed foods were examined by varying the concentrations of purified tropomyosin contained in sample dilution buffers.

(1) Preparation of Sample Dilution Buffer

Purified tropomyosin prepared by the method according to Example 7 was diluted with 20 mM TBS (pH 7.4) to a predetermined concentration, BSA was added to a final concentration of 1%, and then Tween® 20 and Proclin® 200 were added to a final concentration of 0.05%. Model processed foods were measured using the thus obtained sample dilution buffer containing various concentrations of tropomyosin.

(2) Measurement (i) Preparation of Calibration Standard Solution

The ELISA calibration standard solution prepared by the method according to Example 1 was diluted 3420-fold to 1 µg/mL using an extraction reagent for specified ingredient, thereby preparing a calibration standard solution.

The calibration standard solution was diluted 20-fold with the sample dilution buffer containing various concentrations of tropomyosin. Each resultant was subjected to 2-fold serial dilution to 0.78125 ng/mL using the same sample dilution buffer, containing 1/20 v/v of extraction reagent for specified ingredient.

(ii) Preparation of Diluted Solution of Model Processed Food Extract

Model processed food extracts prepared by the method according to Example 1 were diluted 20-fold using sample dilution buffer containing various concentrations of tropomyosin. Furthermore, each resultant was subjected to 2-fold serial dilution to 1/16 using the same sample dilution buffer containing 1/20 v/v of extraction reagent for specified ingredient.

Measurement was performed by the same method as that in Example 2. The percentages (recovery rates) of measured values with respect to the total crustacean protein content in the model processed foods and the dilution linearity of the samples [regression coefficient ($R^2$)] were evaluated.

(3) Results

Table 7 shows the results of measuring model processed foods using sample dilution buffer containing various concentrations of tropomyosin.

TABLE 7

Recovery rates and dilution linearity upon measurement of model processed foods using sample dilution buffer containing various concentrations of tropomyosin

| Purified tropomyosin concentration (w/v) | Fish sausage Recovery rate (%) | $R^2$ | FD egg soup Recovery rate (%) | $R^2$ | Chicken balls Recovery rate (%) | $R^2$ |
|---|---|---|---|---|---|---|
| 0.040% | 86.6 to 129.0 | 0.9940 | 101.7 to 111.8 | 0.9994 | 79.0 to 109.7 | 0.9982 |
| 0.020% | 97.3 to 132.6 | 0.9964 | 107.3 to 124.2 | 0.9995 | 92.0 to 132.5 | 0.9922 |
| 0.010% | 94.4 to 119.8 | 0.9982 | 95.5 to 105.4 | 0.9998 | 89.9 to 114.1 | 0.9962 |
| 0.005% | 94.7 to 104.6 | 0.9968 | 102.2 to 112.4 | 0.9999 | 102.0 to 125.1 | 0.9969 |
| 0.002% | 94.0 to 115.0 | 0.9985 | 103.9 to 124.0 | 0.9993 | 103.4 to 132.1 | 0.9962 |
| 0.001% | 99.0 to 145.4 | 0.9903 | 108.5 to 136.7 | 0.9984 | 108.2 to 149.1 | 0.9953 |

As shown above, the recovery rates of the model processed foods ranged from 79.0% to 149.1% when the tropomyosin concentration ranged from 0.001% to 0.040%. It was revealed that within this range of tropomyosin concentration, good recovery rates could be obtained. Moreover, it was revealed that within a tropomyosin concentration ranging from 0.001% to 0.040%, the dilution linearity upon measurement of the model processed foods was as good as the regression coefficient of $R^2$=0.9903 to 0.9999.

All publications, patents, and patent applications cited herein are incorporated herein by reference in their entirety.

The invention claimed is:

1. An immunoassay method for measuring a Crustacean tropomyosin in a processed food, the method comprising adding purified fish or mammal tropomyosin to an assay solution containing an extract of the processed food, and then measuring the Crustacean tropomyosin in the assay solution by reacting the assay solution with an antibody specific to the Crustacean tropomyosin.

2. The method according to claim 1, wherein the extract of the processed food is prepared by extracting the Crustacean tropomyosin from the processed food with an extraction solution comprising a surfactant and a reducing agent.

3. The method according to claim 1, wherein the concentration of purified fish or mammal tropomyosin contained in the assay solution upon measurement ranges from 0.001% to 0.040%.

* * * * *